(12) United States Patent
Adams et al.

(10) Patent No.: US 6,369,068 B1
(45) Date of Patent: *Apr. 9, 2002

(54) AMINO SUBSTITUTED PYRIMIDINE CONTAINING COMPOUNDS

(75) Inventors: Jerry Leroy Adams, Wayne; Timothy Francis Gallagher, Harleysville; Irennegbe Kelly Osifo, Eagleville; Jeffrey Charles Boehm, King of Prussia, all of PA (US)

(73) Assignee: Smithkline Beecham Corporation, Philadelphia, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/319,859

(22) PCT Filed: Dec. 11, 1997

(86) PCT No.: PCT/US97/23157

§ 371 Date: Jun. 11, 1999

§ 102(e) Date: Jun. 11, 1999

(87) PCT Pub. No.: WO98/25619

PCT Pub. Date: Jun. 18, 1998

Related U.S. Application Data

(63) Continuation-in-part of application No. 08/764,003, filed on Dec. 11, 1996, now Pat. No. 5,739,143, which is a continuation-in-part of application No. 08/659,102, filed on Jun. 3, 1996, now Pat. No. 5,658,903, which is a continuation-in-part of application No. 08/636,779, filed on Apr. 19, 1996, now abandoned, which is a continuation-in-part of application No. 08/473,396, filed on Jun. 7, 1995, now abandoned.
(60) Provisional application No. 60/032,766, filed on Dec. 11, 1996.

(51) Int. Cl.[7] .................... C07D 401/14; A61K 31/506
(52) U.S. Cl. ........................................ 514/275; 544/331
(58) Field of Search .......................... 544/331; 514/275

(56) References Cited

U.S. PATENT DOCUMENTS

| | | | |
|---|---|---|---|
| 3,707,475 A | 12/1972 | Lombardino | 260/309 |
| 3,772,441 A | 11/1973 | Lombardino | 424/273 |
| 3,929,807 A | 12/1975 | Fitzi | 260/298.4 |
| 3,940,486 A | 2/1976 | Fitzi | 424/263 |
| 4,058,614 A | 11/1977 | Baldwin | 424/263 |
| 4,199,592 A | 4/1980 | Cherkofsky | 424/273 R |
| 4,447,431 A | 5/1984 | Sallmann | 424/246 |
| 4,503,065 A | 3/1985 | Wilkerson | 514/396 |
| 4,565,875 A | 1/1986 | Cavender | 548/336 |
| 4,686,231 A | 8/1987 | Bender et al. | 514/333 |
| 4,822,805 A | 4/1989 | Tasasugi et al. | 514/341 |
| 5,593,991 A | 1/1997 | Adams et al. | 514/235.2 |
| 5,593,992 A | 1/1997 | Adams et al. | 514/235.8 |
| 5,658,903 A | 8/1997 | Adams et al. | 514/235.8 |
| 5,663,334 A | 9/1997 | Adams et al. | 544/122 |
| 5,670,527 A | 9/1997 | Adams et al. | 514/341 |
| 5,739,143 A * | 4/1998 | Adams et al. | 514/275 |
| 5,869,660 A | 2/1999 | Adams et al. | 544/122 |

FOREIGN PATENT DOCUMENTS

| | | |
|---|---|---|
| WO | WO92/10190 | 6/1992 |
| WO | WO92/10498 | 6/1992 |
| WO | WO95/02591 | 1/1995 |
| WO | WO 95/09847 | 4/1995 |
| WO | WO 95/09851 | 4/1995 |
| WO | WO 95/09852 | 4/1995 |
| WO | WO 95/09853 | 4/1995 |
| WO | WO 96/21654 | 7/1996 |

OTHER PUBLICATIONS

Dinarello et al., Rev.Infect.Disease, 6, p. 51 (1984).
Dinarello, J.Clin.Immun., 5(5), p. 287–297 (1985).
R.P.Soni, Aust.J.Chem., 35, p. 1493–1496 (1982).
Poli et al., Proc.Nat'l Acad.Sci., 87, p. 782–784 (1990).
VanLeusen et al., J.O.C., 42, p. 1153 (1977).
Kumada et al., Tetrahedron Letters, 22, p. 5319 (1981).
Pridgen, J.Org.Chem., 47, p. 4319 (1982).
Stille, J.Amer.Chem.Soc., 109, p. 5478 (1978).
Fischer et al., Rec.Trav.Chim.Pays.Bas., 84, p. 439 (1965).
Snieckus, V., Tetrahedron Letters, 29, 2135 (1988).
Terashimia, M., Chem.Pharm.Bull., 11, p. 4755 (1985).
Thompson, W.J., et al., J.Org.Chem., 49, p. 5237 (1984).
Garigipati, R., Tetrahedron Letters, 31,p. 1969 (1990).
Engel & Steglich, Liebigs Ann. Chem., 1916 (1978).
Strzybny et al., J. Org. Chem., 28, p. 3381 (1963).
Zavyalov, et al., Khim Farm Zh, 26(3), p. 88 (1992) (With Translation).
Colotta et al., J. Immunol., 132(2), p. 936 (1984).
Simon et al., J. Immunol. Methods, 84, p. 85 (1985).
Becker et al., J. Immunol., 147, p. 4307 (1991).
Gilbert, Synthesis, pp. 30–32 (1972).
Morton et al., Tetrahedron Letters, 4123 (1982).
Armarego, W. J. Chem. Soc., (JCSOA9) p. 561 (1962).

* cited by examiner

Primary Examiner—Richard L. Raymond
Assistant Examiner—Deepak R. Rao
(74) Attorney, Agent, or Firm—Dara L. Dinner; Stephen Venetianer; Charles M. Kinzig

(57) ABSTRACT

Novel 1,4,5-substituted imidazole compounds and compositions for use in therapy as cytokine inhibitors.

11 Claims, No Drawings

AMINO SUBSTITUTED PYRIMIDINE CONTAINING COMPOUNDS

This application is the §371 national stage entry of PCT/US97/23157, filed Dec. 11 1997, which is a continuation in part application of U.S. Ser. No. 08/764,003, now U.S. Pat. No. 5,739,143, filed Dec. 11, 1996, which is a continuation in part application of U.S. Ser. No. 08/659,102, now U.S. Pat. No. 5,658,903, filed Jun. 3, 1996, which is a continuation in part application of U.S. Ser. No. 08/636,779, filed Apr. 19, 1996, abandoned, which is a continuation in part application of U.S. Ser. No. 08/473,396, filed Jun. 7, 1995, abandoned, and which also claims the benefit of provisional application U.S. Ser. No. 60/032,766, filed Dec. 11, 1996.

FIELD OF THE INVENTION

This invention relates to a novel group of imidazole compounds, processes for the preparation thereof, the use thereof in treating cytokine mediated diseases and pharmaceutical compositions for use in such therapy.

BACKGROUND OF THE INVENTION

Interleukin-1 (IL-1) and Tumor Necrosis Factor (TNF) are biological substances produced by a variety of cells, such as monocytes or macrophages. IL-1 has been demonstrated to mediate a variety of biological activities thought to be important in immunoregulation and other physiological conditions such as inflammation [See, e.g., Dinarello et al., *Rev. Infect. Disease*, 6, 51 (1984)]. The myriad of known biological activities of IL-1 include the activation of T helper cells, induction of fever, stimulation of prostaglandin or collagenase production, neutrophil chemotaxis, induction of acute phase proteins and the suppression of plasma iron levels.

There are many disease states in which excessive or unregulated IL-1 production is implicated in exacerbating and/or causing the disease. These include rheumatoid arthritis, osteoarthritis, endotoxemia and/or toxic shock syndrome, other acute or chronic inflammatory disease states such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthrits, rubella arthritis, and acute synovitis. Recent evidence also links IL-1 activity to diabetes and pancreatic β cells.

Dinarello, *J. Clinical Immunology*, 5 (5), 287–297 (1985), reviews the biological activities which have been attributed to IL-1. It should be noted that some of these effects have been described by others as indirect effects of IL-1.

Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, reperfusion injury, graft vs. host reaction, allograft rejections, fever and myalgias due to infection, such as influenza, cachexia secondary to infection or malignancy, cachexia, secondary to acquired immune deficiency syndrome (AIDS), AIDS, ARC (AIDS related complex), keloid formation, scar tissue formation, Crohn's disease, ulcerative colitis, or pyresis.

AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell mediated immunity is impaired and infected individuals manifest severe opportunistic infections and/or unusual neoplasms. HIV entry into the T lymphocyte requires T lymphocyte activation. Other viruses, such as HIV-1, HIV-2 infect T lymphocytes after T Cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication. Monokines, specifically TNF, are implicated in activated T-cell mediated HIV protein expression and/or virus replication by playing a role in maintaining T lymphocyte activation. Therefore, interference with monokine activity such as by inhibition of monokine production, notably TNF, in an HIV-infected individual aids in limiting the maintenance of T cell activation, thereby reducing the progression of HIV infectivity to previously uninfected cells which results in a slowing or elimination of the progression of immune dysfunction caused by HIV infection. Monocytes, macrophages, and related cells, such as kupffer and glial cells, have also been implicated in maintenance of the HIV infection. These cells, like T-cells, are targets for viral replication and the level of viral replication is dependent upon the activation state of the cells. Monokines, such as TNF, have been shown to activate HIV replication in monocytes and/or macrophages [See Poli, et al., Proc. Natl. Acad. Sci., 87:782–784 (1990)], therefore, inhibition of monokine production or activity aids in limiting HIV progression as stated above for T-cells.

TNF has also been implicated in various roles with other viral infections, such as the cytomegalia virus (CMV), influenza virus, and the herpes virus for similar reasons as those noted.

Interleukin-8 (IL-8) is a chemotactic factor first identified and characterized in 1987. IL-8 is produced by several cell types including mononuclear cells, fibroblasts, endothelial cells, and keratinocytes. Its production from endothelial cells is induced by IL-1, TNF, or lipopolysachharide (LPS). Human IL-8 has been shown to act on Mouse, Guinea Pig, Rat, and Rabbit Neutrophils. Many different names have been applied to IL-8, such as neutrophil attractant/activation protein-1 (NAP-1), monocyte derived neutrophil chemotactic factor (MDNCF), neutrophil activating factor (NAF), and T-cell lymphocyte chemotactic factor.

IL-8 stimulates a number of functions in vitro. It has been shown to have chemoattractant propertied for neutrophils, T-lymphocytes, and basophils. In addition it induces histamine release from basophils from both normal and atopic individuals as well as lysozomal enzyme release and respiratory burst from neutrophils. IL-8 has also been shown to increase the surface expression of Mac-1 (CD11b/CD18) on neutrophils without de novo protein synthesis, this may contribute to increased adhesion of the neutrophils to vascular endothelial cells. Many diseases are characterized by massive neutrophil infiltration. Conditions associated with an increased in IL-8 production (which is responsible for chemotaxis of neutrophil into the inflammatory site) would benefit by compounds which are suppressive of IL-8 production.

IL-1 and TNF affect a wide variety of cells and tissues and these cytokines as well as other leukocyte derived cytokines are important and critical inflammatory mediators of a wide variety of disease states and conditions. The inhibition of these cytokines is of benefit in controlling, reducing and alleviating many of these disease states.

There remains a need for treatment, in this field, for compounds which are cytokine suppressive anti-inflammatory drugs, i.e. compounds which are capable of inhibiting cytokines, such as IL-1, IL-6, IL-8 and TNF.

SUMMARY OF THE INVENTION

This invention relates to the novel compounds as described herein, and pharmaceutical compositions comprising these compounds and a pharmaceutically acceptable diluent or carrier.

In particular the present invention relates to a method of treating a CSBP/RK/p38 kinase mediated disease, in a mammal in need thereof which comprises administering to said mammal an effective amount of a novel compound as described herein.

This invention also relates to a method of inhibiting cytokines and the treatment of a cytokine mediated disease, in a mammal in need thereof which comprises administering to said mammal an effective amount of a novel compound as described herein.

This invention more specifically relates to a method of inhibiting the production of IL-1 in a mammal in need thereof which comprises administering to said mammal an effective amount of a novel compound as described herein.

This invention more specifically relates to a method of inhibiting the production of IL-8 in a mammal in need thereof which comprises administering to said mammal an effective amount of a novel compound as described herein.

This invention more specifically relates to a method of inhibiting the production of TNF in a mammal in need thereof which comprises administering to said mammal an effective amount of a novel compound as described herein.

DETAILED DESCRIPTION OF THE INVENTION

The novel compounds of the present invention are:
4-(4-Thiomethylphenyl-5-[(2-(phenyl)amino)pyrimidin-4-yl]-1-(1-ethoxycarbonylpiperidin-4-yl)imidazole
4-(4-Thiomethylphenyl-5-[(2-(phenyl)amino)pyrimidin-4-yl]-1-(piperidin-4-yl)imidazole
4-(4-Methylsulfinylphenyl-5-[(2-(phenyl)amino)pyrimidin-4-yl]-1-(piperidin-4-yl)imidazole
4-(4-Fluorophenyl-5-[(2-(4-fluorophenyl)amino)pyrimidin-4-yl]-1-(piperidin-4-yl)imidazole
4-(4-Fluorophenyl-5-[(2-(3-fluorophenyl)amino)pyrimidin-4-yl]-1-(piperidin-4-yl)imidazole
4-(4-Fluorophenyl-5-[(2-(2-fluorophenyl)amino)pyrimidin-4-yl]-1-(piperidin-4-yl)imidazole
4-(4-Fluorophenyl-5-[(2-(4-benzyloxyphenyl)amino)pyrimidin-4-yl]-1-(1-ethoxycarbonylpiperidin-4-yl)imidazole
4-(4-Fluorophenyl-5-[(2-(3-benzyloxyphenyl)amino)pyrimidin-4-yl]-1-(1-ethoxycarbonylpiperidin-4-yl)
4-(4-Fluorophenyl-5-[(2-(3-trifluoromethylphenyl)amino)pyrimidin-4-yl]-1-(piperidin-4-yl)imidazole
4-(4-Fluorophenyl-5-[(2-(3,4-difluorophenyl)amino)pyrimidin-4-yl]-1-(piperidin-4-yl)imidazole
4-(4-Fluorophenyl-5-[(2-(4-hydroxyphenyl)amino)pyrimidin-4-yl]-1-(piperidin-4-yl)imidazole
4-(4-Fluorophenyl-5-[(2-(3-hydroxyphenyl)amino)pyrimidin-4-yl]-1-(piperidin-4-yl)imidazole
4-(4-Fluorophenyl-5-[(2-(4-methoxyphenyl)amino)pyrimidin-4-yl]-1-(piperidin-4-yl)imidazole
4-(4-Fluorophenyl-5-[(2-(3-methoxyphenyl)amino)pyrimidin-4-yl]-1-(piperidin-4-yl)imidazole
4-(4-Fluorophenyl-5-[(2-(2-methoxyphenyl)amino)pyrimidin-4-yl]-1-(piperidin-4-yl)imidazole
4-(4-Fluorophenyl-5-[(2-(3-fluoro-2-methylphenyl)amino)pyrimidin-4-yl]-1-(piperidin-4-yl)imidazole
4-(4-Fluorophenyl-5-[(2-(3-chlorophenyl)amino)pyrimidin-4-yl]-1-(piperidin-4-yl)imidazole
4-(4-Fluorophenyl-5-[(2-(4-chlorophenyl)amino)pyrimidin-4-yl]-1-(piperidin-4yl)imidazole
4-(4-Fluorophenyl-5-[(2-(4-trifluoromethylphenyl)amino)pyrimidin-4-yl]-1-(piperidin-4-yl)imidazole
4-(4-Fluorophenyl-5-[(2-(3,4-dichlorophenyl)amino)pyrimidin-4-yl]-1-(piperidin-4-yl)imidazole
4-(4-Fluorophenyl-5-[(2-(4-fluoro-2-methylphenyl)amino)pyrimidin-4-yl]-1(piperidin-4-yl)imidazole
4-(4-Fluorophenyl-5-[(2-(5-fluoro-2-methylphenyl)amino)pyrimidin-4-yl]-1-(piperidin-4-yl)imidazole
4-(4-Fluorophenyl-5-[(2-(4-fluoro-2,6-dimethylphenyl)amino)pyrimidin-4-yl]-1-(piperidin-4-yl)imidazole
4-(4-Fluorophenyl-5-[(2-(4-fluoro-2-chlorophenyl)amino)pyrimidin-4-yl]-1-(piperidin-4-yl)imidazole
trans 4-(4-Fluorophenyl-5-[(2-(4-fluoro-2-methylphenyl)amino)pyrimidin-4-yl]-1-(4-hydroxycyclohexyl)imidazole
trans 4-(4-Fluorophenyl-5-[(2-(4-fluorophenyl)amino)pyrimidin-4-yl]-1-(4-hydroxycyclohexyl)imidazole
trans 4-(4-Fluorophenyl-5-[(2-(3-fluoro-2-methylphenyl)amino)pyrimidin-4-yl]-1-(4-hydroxycyclohexyl)imidazole
trans 4-(4-Fluorophenyl-5-[(2-(5-fluoro-2-methylphenyl)amino)pyrimidin-4-yl]-1(4-hydroxycyclohexyl)imidazole
trans 4-(4-Fluorophenyl-5-[(2-(4-fluoro-2-chlorophenyl)amino)pyrimidin-4-yl]-1-(4-hydroxycyclohexyl)imidazole
cis 4(4-Fluorophenyl-5-[(2-(4-fluoro-2-methylphenyl)amino)pyrimidin-4-yl]-1-(4-hydroxycyclohexyl)imidazole
cis 4-(4-Fluorophenyl-5-[(2-(4-fluorophenyl)amino)pyrimidin-4-yl]-1-(4-hydroxycyclohexyl)imidazole
cis 4-(4-Fluorophenyl-5-[(2-(3-fluoro-2-methylphenyl)amino)pyrimidin-4-yl]-1-(4-hydroxycyclohexyl)imidazole
cis 4-(4-Fluorophenyl-5-[(2-(5-fluoro-2-methylphenyl)amino)pyrimidin-4-yl]-1-(4-hydroxycyclohexyl)imidazole
cis 4-(4-Fluorophenyl-5-[(2-(4-fluoro-2-chlorophenyl)amino)pyrimidin-4-yl]-1-(4-hydroxycyclohexyl)imidazole
trans 4-(4-Fluorophenyl-5-[(2-(4-fluoro-2-methylphenyl)amino)pyrimidin-4-yl]-1-(4-hydroxy-4-methylcyclohexyl)imidazole
trans 4-(4-Fluorophenyl-5-[(2-(4-fluorophenyl)amino)pyrimidin-4-yl]-1-(4-hydroxy-4-methylcyclohexyl)imidazole
trans 4-(4-Fluorophenyl-5-[(2-(3-fluoro-2-methylphenyl)amino)pyrimidin-4-yl]-1-(4-hydroxy-4-methylcyclohexyl)imidazole
trans 4-(4-Fluorophenyl-5-[(2-(5-fluoro-2-methylphenyl)amino)pyrimidin-4-yl]-1-(4-hydroxy-4-methylcyclohexyl)imidazole
trans 4-(4-Fluorophenyl-5-[(2-(4-fluoro-2-chlorophenyl)amino)pyrimidin-4-yl]-1-(4-hydroxy-4-methylcyclohexyl)imidazole
cis 4-(4-Fluorophenyl-5-[(2-(4-fluoro-2-methylphenyl)amino)pyrimidin-4-yl]-1-(4-hydroxy-4-methylcyclohexyl)imidazole cis 4-(4-Fluorophenyl-5-[(2-(4-fluorophenyl)amino)
pyrimidin-4-yl]-14-hydroxy-4-methylcyclohexyl)
imidazole cis 4-(4-Fluorophenyl-5-[(2-(3-fluoro-2-methylphenyl)
amino)pyrimidin-4-yl]-1-(4-hydroxy-4-
methylcyclohexyl)imidazole cis 4-(4-Fluorophenyl-5-[(2-(5-fluoro-2-methylphenyl)
amino)pyrimidin-4-yl]-1-(4-hydroxy-4-
methylcyclohexyl)imidazole cis 4-(4-Fluorophenyl-5-[(2-(4-fluoro-2-chlorophenyl)
amino)pyrimidin-4-yl]-(4-hydroxy-4-methylcyclohexyl)
imidazole;

or a pharmaceutically acceptable salt thereof.

Pharmaceutically acid addition salts of these may be obtained in known manner, for example by treatment thereof with an appropriate amount of acid in the presence of a suitable solvent.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of the novel compound described herein may also be formed with a pharmaceutically acceptable cation, for instance, if a substituent group comprises a carboxy moiety, Suitable pharmaceutically acceptable cations are well known to those skilled in the art and include alkaline, alkaline earth, ammonium and quaternary ammonium cations.

It is recognized that the compounds of the present invention may exist as stereoisomers, regioisomers, or diastereiomers. These compounds may contain one or more asymmtric carbon atoms and may exist in racemic and optically active forms. All of these compounds are included within the scope of the present invention.

The compounds herein are generically described in U.S. Pat. No. 5,658,903 for use as CSBP/RK/p38 inhibitors. The compounds may be prepared as described below in the Synthetic Examples Section, or they may be prepared by analagous methods to those described in U.S. Pat. No. 5,658,903, whose disclosure is incorporated herein by reference in its entirety.

Therefore, another aspect of the present invention are analogy processes of making the novel compounds as described herein, using the methods as described in U.S. Pat. No. 5,658,903, which is incorporated by reference herein in its entirety.

The compounds herein, or pharmaceutically acceptable salt thereof, can be used in the manufacture of a medicament for the prophylactic or therapeutic treatment of any disease state in a human, or other mammal, which is exacerbated or caused by excessive or unregulated cytokine production by such mammal's cell, such as but not limited to monocytes and/or macrophages, or by excessive or unregulated CSBP/RK/p38 production.

These compounds are capable of inhibiting proinflammatory cytokines, such as IL-1, IL-6, IL-8 and TNF and are therefore of use in therapy. IL-1, IL-6, IL-8 and TNF affect a wide variety of cells and tissues and these cytokines, as well as other leukocyte-derived cytokines, are important and critical inflammatory mediators of a wide variety of disease states and conditions. The inhibition of these pro-inflammatory cytokines is of benefit in controlling, reducing and alleviating many of these disease states.

Accordingly, the present invention provides a method of treating a cytokine-mediated disease which comprises administering an effective cytokine-interfering amount of a novel compound as described herein, or a pharmaceutically acceptable salt thereof.

These compounds are capable of inhibiting inducible proinflammatory proteins, such as COX-2, also referred to by many other names such as prostaglandin endoperoxide synthase-2 (PGHS-2) and are therefore of use in therapy. These proinflammatory lipid mediators of the cyclooxygenase (CO) pathway are produced by the inducible COX-2 enzyme. Regulation, therefore of COX-2 which is responsible for the these products derived from arachidonic acid, such as prostaglandins affect a wide variety of cells and tissues are important and critical inflammatory mediators of a wide variety of disease states and conditions. Expression of COX-1 is not effected by these compounds. This selective inhibition of COX-2 may alleviate or spare ulcerogenic liability associated with inhibition of COX-1 thereby inhibiting prostoglandins essential for cytoprotective effects. Thus inhibition of these pro-inflammatory mediators is of benefit in controlling, reducing and alleviating many of these disease states. Most notably these inflammatory mediators, in particular prostaglandins, have been implicated in pain, such as in the sensitization of pain receptors, or edema. This aspect of pain management therefore includes treatment of neuromuscular pain, headache, cancer pain, and arthritis pain. Therefore, the novel compounds herein are of use in the prophylaxis or therapy in a human, or other mammal, by inhibition of the synthesis of the COX-2 enzyme.

Accordingly, the present invention provides a method of inhibiting the synthesis of COX-2 which comprises administering an effective amount of a novel compound as described herein. The present invention also provides for a method of prophylaxis treatment in a human, or other mammal, by inhibition of the synthesis of the COX-2 enzyme.

A new member of the MAP kinase family, alternatively termed CSBP, p38, or RK, has been identified independently by several laboratories recently. See for instance, patent application U.S. Ser. No. 08/123,175 Lee et l., filed September 1993, USSN; Lee et al., PCT 94/10529 filed Sep. 16, 1994, and Lee et al., Nature 300, n(72), 739–746 (December 1994). Activation of this novel protein kinase via dual phosphorylation has been observed in different cell systems upon stimulation by a wide spectrum of stimuli, such as physicochemical stress and treatment with lipopolysaccharide or proinflammatory cytokines such as interleukin-1 and tumor necrosis factor. The cytokine biosynthesis inhibitors of the present invention have been determined to be potent and selective inhibitors of CSBP/p38/RK kinase activity. These inhibitors are of aid in determining the signaling pathways involvement in inflammatory responses. In particular, for the first time a definitive signal transduction pathway can be prescribed to the action of lipopolysaccharide in cytokine production in macrophages.

The cytokine inhibitors were subsequently tested in a number of animal models for anti-inflammatory activity. Model systems were chosen that were relatively insensitive to cyclooxygenase inhibitors in order to reveal the unique activities of cytokine suppressive agents. The inhibitors exhibited significant activity in many such in vivo studies. Most notable are its effectiveness in she collagen-induced arthritis model and inhibition of TNF production in the endotoxic shock model. In the latter study, the reduction in plasma level of TNF correlated with survival and protection from endotoxic shock related mortality. Also of great importance are the compounds effectiveness in inhibiting bone resorption in a rat fetal long bone organ culture system. Griswold et al., (1988) *Arthritis Rheum.* 31:1406–1412; Badger, et al., (1980) *Circ. Shock* 27, 51–61; Votta et al., (1994) in vitro. *Bone* 15, 533–538; Lee et al., (1993). B *Ann. N. Y. Acad Sci.* 696, 149–170.

Another aspect of the present invention, therefore, is the treatment of a CSBP/RK/p38 kinase mediated disease, in a mammal in need thereof, which comprises administering to said mammal an effective amount of a compound as described herein. Suitable diseases, include those mentioned herein for IL-1, IL-6, IL-8 and TNF and more specifically those disease which are CSBP/RK/p38 kinase mediated diseases. These include, but are not limited to psoriatic arthritis, Reiter's syndrome, rheumatoid arthritis, gout, traumatic arthritis, rubella arthritis, acute synovitis, rheumatoid arthritis, rheumatoid spondylitis, osteoarthritis, gouty arthritis and other arthritic condition, sepsis, septic shock, endotoxic shock, gram negative sepsig, toxic shock gyndrome, asthma, adult respiratory distress syndrome, chronic pulmonary inflammatory disease silicosis, pulmonary sarcososis, Alzheimer's disease, stroke, neurotrauma, reperfusion injury, CNS injuries, such as neurotrauma and ischemia, including both open and closed head injuries), restenosis, such as occurs following coronary angioplasty, cardiac and renal reperfusion injury, thrombosis, glomerularnephritis, cerebral malaria, chronic pulmonary inflammatory disease, bone resorption diseases, osteoporosis, graft vs. host reaction, allograft rejections, diabetes, Crohn's disease, ulcerative colitis or any other anti-inflammatory bowel disease (IBD), psoriasis, eczema, contact dermnatitis, psoriasis, pyresis, sunburn, conjunctivitis, multiple sclerosis, or muscle degeneration.

CNS injuries as defined herein include both open or penetrating head trauma, such as by surgery, or a closed head trauma injury, such as by an injury to the head region. Also included within this definition is ischemic stroke, particularly to the brain area.

Ischemit stroke may be defined as a focal neurologic disorder that results from insufficient blood supply to a particular brain area, usually as a consequence of an embolus, thrombi, or local atheromatous closure of the blood vessel. The role of inflammatory cytokines in this are has been emerging and the present invention provides a mean for the potential treatment of these injuries. Relatively little treatment, for an acute injury such as these has been available.

TNF-α is a cytokine with proinflammator actions, including endothelial leukocyte adhesion molecule expression, Leukocytes infiltrate into igchemic brain lesions and hence compounds which inhibit or decrease levels of TNF would be useful for treatment of ischemic brain injury. See Liu et al., Stoke, Vol. 25., No. 7, pp 1481–88 (1994) whose disclosure is incorporated herein by reference.

Models of closed head injuries and treatment with mixed 5-LO/CO agents is discussed in Shohami et al., J. of Vaisc & Clinical Physiology and Pharmacology, Vol. 3, No. 2, pp. 99–107 (1992) whose disclosure is incorporated herein by reference. Treatment which reduced edema formation was found to improve functional outcome in those animals treated.

In particular, the novel compounds described herein are of use in the prophylaxis or therapy of any disease state in a human, or other mammal, which is exacerbated by or caused by excessive or unregulated IL-1, IL-8 or TNF production by such mammal's cell, such as, but not limited to, monocytes and/or macrophages.

Accordingly, in another aspect, this invention relates to a method of inhibiting the production of IL-1 in a mammal in need thereof which comprises administering to said mammal an effective amount of a novel compound as described herein.

There are many disease states in which excessive or unregulated IL-1 production is implicated in exacerbating and/or causing the disease. These include rheumatoid arthritis, osteoarthritis, stroke, endotoxemia and/or toxic shock syndrome, other acute or chronic inflammatory disease states such as the inflammatory reaction induced by endotoxin or inflammatory bowel disease, tuberculosis, atherosclerosist, muscle degeneration, multiple sclerosis, cachexia, bone resorption, psoriatic arthritis, Reiter's syndrome, rheumatoid arthritis, gout, traumatic arthritis, rubella arthritis and acute synovitis. Recent evidence also links IL-1 activity to diabetes, pancreatic β cells and Alzheimer's disease.

In a further aspect, this invention relates to a method of inhibiting the production of TNF in a mammal in need thereof which comprises administering to said mammal an effective amount of a of a novel compound as described herein.

Excessive or unregulated TNF production has been implicated in mediating or exacerbating a number of diseases including rheumatoid arthritis, rheumatoid spondylitis, osteoarthritis, gouty arthritis and other arthritic conditions, sepsis, septic shock, endotoxic shock, gram negative sepsis, toxic shock syndrome. adult respiratory distress syndrome, stroke, cerebral malaria, chronic pulmonary inflammatory disease, silicosis, pulmonary sarcoisosis, bone resorption diseases, such as osteoporosis, reperfusion injury, graft vs. host reaction, allograft rejections, fever and myalgias due to infection, such as influenza, cachexia secondary to infection or malignancy, cachexia secondary to acquired immune deficiency syndrome (AIDS), AIDS, ARC (AIDS related complex), keloid formation, scar tissue formation, Crohn's disease, ulcerative colitis and pyresis.

These compounds are also useful in the treatment of viral infections, where such viruses are sensitive to upregulation by TNF or will elicit TNF production in vivo. The viruses contemplated for treatment herein are those that produce TNF as a result of infection, or those which are sensitive to inhibition, such as by decreased replication, directly or indirectly, by the TNF inhibiting-compounds described herein. Such viruses include, but are not limited to HIV-1, HIV-2 and HIV-3, Cytomegalovirus (CMV), Influenza, adenovirus and the Herpes group of viruses, such as but not limited to, Herpes Zoster and Herpes Simplex.

The novel compounds described herein may also be used in association with the veterinary treatment of mammals, other than in humans, in need of inhibition of TNF production. TNF mediated diseases for treatment, therapeutically or prophylactically, in animals include disease states such as those noted above, but in particular viral infections. Examples of such viruses include, but are not limited to, lentivirus infections such as, equine infectious anaemia virus, caprine arthritis virus, visna virus, or maedi virus or retrovirus infections, such as but not limited to feline irnmunodeficiency virus (FIV), bovine immunodeficiency virus, or canine immunodeficiency virus or other retroviral infections.

The compounds may also be used topically in the treatment or prophylaxis of topical disease states mediated by or exacerbated by excessive cytokine production, such as by IL-1 or TNF respectively, such as inflamed joints, eczema, psoriasis and other inflammatory skin conditions such as sunburn; inflammatory eye conditions including conjunctivitis; pyresis, pain and other conditions associated with inflammation.

These compounds may also be useful to inhibit the production of IL-8 (Interleukin-8, NAP). Accordingly, in a further aspect, this invention relates to a method of inhibiting the production of IL-8 in a mammal in need thereof which comprises administering to said mammal an effective amount of a compound as described herein.

There are many disease states in which excessive or unregulated IL-8 production is implicated in exacerbating and/or causing the disease. These diseases are characterized by massive neutrophil infiltration such as, psoriasis, inflammatory bowel disease, asthma, cardiac and renal reperfusion injury, adult respiratory distress syndrome, thrombosis and glomerulonephritis. All of these diseases are associated with increased IL-8 production which is responsible for the chemotaxis of neutrophils into the inflammatory site. In contrast to other inflammatory cytokines (IL-1, TNF, and IL-6), IL-8 has the unique property of promoting neutrophil chemotaxis and activation. Therefore, the inhibition of IL-8 production would lead to a direct reduction in the neutrophil infiltration.

The compounds herein are administered in an amount sufficient to inhibit cytokine, in particular IL-1, IL-6, IL-8 or TNF, production such that it is regulated down to normal levels, or in some case to subnormal levels, so as to ameliorate or prevent the disease state. Abnormal levels of IL-1, IL-6, IL-8 or TNF, for instance in the context of the present invention, constitute: (i) levels of free (not cell bound) IL-1, IL-6, IL-8 or TNF greater than or equal to 1 picogram per ml; (ii) any cell associated IL-1, IL-6, IL-8 or TNF; or (iii) the presence of IL-1, IL-6, IL-8 or TNF mRNA above basal levels in cells or tissues in which IL-1, IL-6, IL-8 or TNF, respectively, is produced.

The discovery that the compounds herein are inhibitors of cytokines, specifically IL-1, IL-6, IL-8 and TNF is based upon the effects of these compounds on the production of the IL-1, IL-8, TNF, and CSBP kinase, in the in vitro assays which are described herein.

As used herein, the term "inhibiting the production of IL-1 (IL-6, IL-8 or TNF)" refers to:
a) a decrease of excessive in vivo levels of the cytokine (IL-1, IL-6, IL-8 or TNF) in a human to normal or sub-normal levels by inhibition of the in vivo release of the cytokine by all cells, including but not limited to monocytes or macrophages;
b) a down regulation, at the genomic level, of excessive in vivo levels of the cytokine (IL-1, IL-6, IL-8 or TNF) in a human to normal or sub-normal levels,
c) a down regulation, by inhibition of the direct synthesis of the cytokine (IL-1, IL-6, IL-8 or TNF) as a postranslational event; or
d) a down regulation, at the translational level, of excessive in vivo levels of the cytokine (IL-1, IL-6, IL-8 or TNF) in a human to normal or sub-normal levels.

As used herein, the term "TNF mediated disease or disease state" refers to any and all disease states in which TNF plays a role, either by production of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disease stated mediated by TNF.

As used herein, the term "cytokine" refers to any secreted polypeptide that affects the functions of cells and is a molecule which modulates interactions between cells in the immune, inflammatory or hematopoietic response. A cytokine includes, but is not limited to, monokines and lymphokines, regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to, Interleukin-1 (IL-1), Interleukin-6 (IL-6), Interleukin-8 (IL-8), Tumor Necrosis Factor-alpha (TNF-α) and Tumor Necrosis Factor beta (TNF-β).

As used herein, the term "cytokine interfering" or "cytokine suppressive amount" refers to an effective amount of a compound which will cause a decrease in the in vivo levels of the cytokine to normal or sub-normal levels, when given to a patient for the prophylaxis or treatment of a disease state which is exacerbated by, or caused by, excessive or unregulated cytokine production.

As used herein, the cytokine referred to in the phrase "inhibition of a cytokine, for use in the treatment of a HIV-infected human" is a cytokine which is implicated in (a) the initiation and/or maintenance of T cell activation and/or activated T cell-mediated HIV gene expression and/or replication and/or (b) any cytokine-mediated disease associated problem such as cachexia or muscle degeneration.

As TNF-β (also known as lymphotoxin) has close structural homology with TNF-α (also known as cachectin) and since each induces similar biologic responses and binds to the same cellular receptor, both TNF-a and TNF-β are inhibited by the compounds of the present invention and thus are herein referred to collectively as "TNF" unless specifically delineated otherwise.

In order to use a compound, or a pharmaceutically acceptable salt thereof in therapy, it will normally be formulated into a pharmaceutical composition in accordance with standard pharmaceutical practice. This invention, therefore, also relates to a pharmaceutical composition comprising an effective, non-toxic amount of a novel compound, as described herein, and a pharmaceutically acceptable carrier or diluent.

The compounds, pharmaceutically acceptable salts thereof and pharmaceutical compositions incorporating such may conveniently be administered by any of the routes conventionally used for drug administration, for instance, orally, topically, parenterally or by inhalation. Those the compounds may be administered in conventional dosage forms prepared by combining a compound with standard pharmaceutical carriers according to conventional procedures. The compounds may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

The compounds may be administered topically, that is by non-systemic administration. This includes the application of a compound externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or nonaqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compounds may be administered parenterally, that is by intravenous, intramuscular, subcutaneous intranasal, intrarectal, intravaginal or intraperitoneal administration. The subcutaneous and intramuscular forms of parenteral admnistration are generally preferred. Appropriate dosage forms for such administration may be prepared by conventional techniques. Compounds may also be administered by inhalation, that is by intranasal and oral inhalation administration. Appropriate dosage forms for such administration, such as an aerosol formulation or a metered dose inhaler, may be prepared by conventional techniques.

For all methods of use disclosed herein for the compounds, the daily oral dosage regimen will preferably be from about 0.01 to about 80 mg/kg of total body weight, preferably from about 0.1 to 30 mg/kg, more preferably from about 0.2 mg to 15 mg. The daily parenteral dosage regimen about 0.01 to about 80 mg/kg of total body weight, preferably from about 0.1 to about 30 mg/kg, and more preferably from about 0.2 mg to 15 mg/kg. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compounder a pharmaceutically acceptable salt thereof, will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound given per day for a defined number of days, can be ascertained by those skilled in the art using conventional course of treatment determination tests.

The novel compounds may also be used in association with the veterinary treatment of mammals, other than humans, in need of inhibition of cytokine inhibition or production. In particular, cytokine mediated diseases for treatment, therapeutically or prophylactically, in animals include disease states such as those noted herein in the Methods of Treatment section, but in particular viral infections. Examples of such viruses include, but are not limited to, lentivirus infections such as, equine infectious anaemia virus, caprine arthritis virus, visna virus, or maedi virus or retrovirus infections, such as but not limited to feline immunodeficiency virus (FIV), bovine immunodeficiency virus, or canine inmmunodeficiency virus or other retroviral infections.

The invention will now be described by reference to the following biological examples which are merely illustrative and are not to be construed as a limitation of the scope of the present invention.

BIOLOGICAL EXAMPLES

The cytokine-inhibiting effects of compounds of the present invention were determined by in vitro assays for Interleukin-1 (IL-1), Tumour Necrosis Factor (TNF), In vivo TNF, Interleukin-8 (IL-8),: Cytokine Specific Binding Protein, CSBP Kinase, Prostoglandin endoperoxide synthase-2 (PGHS-2), TNF-α in Traumatic Brain Injury Assay, and CNS Injury model for IL-β mRNA. These assays are all described in detail in U.S. Pat. No. 5,658,903.

While the CSBP Kinase assay is described in U.S. Pat. No. 5,658,903 it is repeated below.

CSBP Kinase Assay

This assay measures the CSBP-catalyzed transfer of $^{32}P$ from $[a-^{32}P]ATP$ to threonine residue in an epidermal growth factor receptor (EGPR)-derived pepide (T669) with the following sequence: KRELVEPLTPSGEAPNQALLR (residues 661–681). (See Gallagher et al., "Regulation of Stress Induced Cytokine Production by Pyridinyl Imidazoles: Inhibition of CSPB Kinase", BioOrganic & Medicinal Chemistry, to be published 1996).

Kinase reactions (total volume 30 ul) contain: 25 mM Hepes buffer, pH 7.5; 10 mM $MgCl_2$; 170 uM ATP[(1)]; 10 uM Na ortho vanadate; 0.4 mM T669 peptide; and 20–80 ng of yeast-expressed purified CSBP2 (see Lee et al., *Nature* 300, n(72), 739–746 (December 1994)). Compounds (5 ul from [6×] stock[(2)]) are pre-incubated with the enzyme and peptide for 20 min. on ice prior to starting the reactions with 32P/MgATP. Reactions are incubated at 30° C. for 10 min. and stopped by adding 10 ul of 0.3 M phosphoric acid. 32P-labeled peptide is separated on phosphocellulose (Wattman, p81) filters by spotting 30 ul reaction mixture. Filters are washed 3 times with 75 mM phosphoric acid followed by 2 washes with $H_2O$, and counted for 32P.

[(1)] The Km of CSBP for ATP was determined to be 170 uM. Therefore, compounds screened at the Km value of ATP.
[(2)] Compounds are usually dissolved in DMSO and are diluted in 25 mM Hepes buffer to get final concentration of DMSO of 0.17%.

Examples 1 to 15, herein, have all demonstrated positive inhibitory activity of an $IC_{50}$ of <50 uM in this kinase assay.

SYNTHETIC EXAMPLES

The invention will now be described by reference to the following examples which are merely illustrative and are not to be construed as a limitation of the scope of the present invention. All temperatures are given in degrees centigrade, all solvents are highest available purity and all reactions run under anhydrous conditions in an argon atmosphere unless otherwise indicated.

In the Examples, all temperatures are in degrees Centigrade (°C.). Mass spectra were performed upon a VG Zab mass spectrometer using fast atom bombardment, unless otherwise indicated. $^{1}$H-NMR (hereinafter "NMR") spectra were recorded at 250 MHz using a Bruker AM 250 or Am 400 spectrometer. Multiplicities indicated are: s=singlet, d=doublet, t=triplet, q=quartet, m=multiplet and br indicates a broad signal. Sat. indicates a saturated solution, eq indicates the proportion of a molar equivalent of reagent relative to the principal reactant. Flash Chromatography is run over a Merck Silica gel 60 (230–400 mesh).

Example 1
4-(4-Thiomethylphenyl-5-[(2-(phenyl)amino)pyrimidin-4-yl]-1-(piperidin-4-yl)imidazole

[5-(2-phenylamino-4-pyrimidinyl)-4-(4-fluorophenyl)-1-(4-piperidinyl)imidazole; 500 mg, 1.21 mmol], as produced in accordance with Example 19 of U.S. Pat. No. 5,658,903, and sodiumthiomethoxide (254 mg, 3.6 mmol) were dissolved in DMF. The resulting mixture was stirred for 18 hours at 90° C. Most of DMF were evaporated in high vacuo. Poured into water and extracted with EtOAc. The extracts were washed with $NaHCO_3$, brine, dried with $Na_2SO_4$, and concentrated to a white solid. Recrystallized from EtOAc/Hexane (1:9) to afford the titled compound (300 mg). ESP+ (Mass Spec) m/z 443 (MH+).

Example 2
4-(4-Methylsulfinylphenyl-5-[(2-(phenyl)amino)pyrimidin-4-yl]-1-(piperidin-4-yl)imidazole The product of the previous example (300 mg, 0.68 mmol) was dissolved in THF cooled to −10° and oxone (417 mg, 0.68 mmol) in water (5 ml) was added dropwise (T<5° C.). The resulting mixture was warmed to 20° C. over 50 minutes, poured into a vigorously stirred mixture of 10% aqueous NaOH (50 ml), and EtOAc was separated, dried ($Na_2SO_4$, and concentrated to a white solid. Recrystallized from EtOAc/Hexane (1:10) to afford the titled compound (200 mg). mp=190–193° C.

Example 3
4-(4-Fluorophenyl-5-[(2-(4-fluorophenyl)amino)pyrimidin-4-yl]-1-(pipendin-4yl)imidazole a) 4-(4-Fluorophenyl-5-[(2-(4-fluorophenylamino)pyrimidin-4-yl]-1-[(1-t-butoxycarbonyl)piperidin-4-yl]imidazle Using an aluminum amide reagent as prepared by the procedure of Example 15 in U.S. Pat. No. 5,658,903, except substituting 4-fluoroaniline for 3-bromoaniline and reacting with 5-(2-methylsulfinyl-4-pyrimidinyl)-4-(4-fluorophenyl)-1-[(1-t-butoxycarbonyl)-4-piperidinyl]imidazole [prepared in accordance with Example 19 (c) of U.S. Pat. No. 5,658,903,] and using the general procedure as further outlined above in Example 15 to afford the title compound.

b) 4-(4-Fluorophenyl-5-[(2-(4-fluorophenyl)amino)pyrimidin-4-yl]-1-(piperidin-4-yl)imidazole The product of the previous step was treated according to procedure 19 (e) of U.S. Pat. No. 5,658,903, to afford the title compound. ES+MS m/z=433 (M$^{+}$+H).

Example 4
4-(4-Fluorophenyl-5-[(2-(3-fluorophenyl)amino)pyrimidin-4-yl]-1-(piperidin-4-yl)imidazole The title compound was prepared using the general procedure outlined in Example 3 (a) & (b), above, but substituting 3-fluoroaniline as the aniline component. ES+MS m/z=433 (M$^{+}$+H).

Example 5
4-(4-Fluorophenyl-5-[(2-(2-fluorophenyl)amino)pyrimidin-4-yl]-1-(piperidin-4-yl)imidazole The title compound was prepared using the general procedure outlined in Example 3 (a) & (b), above but substituting 2-fluoroaniline as the aniline component. ES+MS m/z=433 (M$^{+}$+H).

Example 6
4-(4-Fluorophenyl-5-[(2-(4-benzyloxyphenyl)amino)pyrimidin-4-yl]-1-(N-carboethoxypiperidin-4-yl)imidazole The title compound was prepared using the general procedure as outlined in accordance with Example 20(c) of U.S. Pat. No. 5,658,903, but substituting 4-benzyloxyphenylguanidine as the guanidine component. ES+MS m/z=593 (M$^{+}$+H).

Example 7
4-(4-Fluorophenyl-5-[(2-(3-benzyloxyphenyl)amino)pyrimidin-4-yl]-1-(N-carboethoxypiperidin-4-yl)imidazole The title compound was prepared using the general procedure outlined in accordance with Example 20(c) of U.S.

Pat. No. 5,658,903, but substituting 3-benzyloxyphenylguanidine as the guanidine component. ES+MS m/z=593 (M++H).

Example 8

4-(4-Fluorophenyl-5-[(2-(3-trifluoromethylphenyl)amino)pyrimidin-4-yl]-1-(piperidin-4-yl)imidazole The title compound was prepared using the general procedure outlined in accordance with Example 20(c) of U.S. Pat. No. 5,658,903, but substituting 3-trifluoromethylphenylguanidine as the guanidine component. ES+MS m/z=483 (M++H).

Example 9

4-(4-Fluorophenyl-5-[(2-(3,4-difluorophenyl)amino)pyrimidin-4-yl]-1-(piperidin-4-yl)imidazole The title compound was prepared using the general procedure outlined in accordance with Example 20 (c) of U.S. Pat. No. 5,658,903, but substituting 3,4-difluorophenylguanidine as the guanidine component. ES+MS m/z=451 (M++H).

Example 10

4-(4-Fluorophenyl-5-[(2-(4-hydroxyphenyl)amino)pyrimidin-4-yl]-1-(piperidin-4-yl)imidazole The product of Example 6 [4-(4-Fluorophenyl-5-[(2-(4-benzyloxyphenyl)amino)pyrimidin-4-yl]-1-(N-carboethoxypiperidin-4-yl)imidazole] was treated according to the procedure of Example 20 (d) of U.S. Pat. No. 5,658,903 to afford the title compound. ES+MS m/z=431 (M++H).

Example 11

4-(4-Fluorophenyl-5-[(2-(3-hydroxyphenyl)amino)pyrimidin-4-yl]-1-(piperidin-4-yl)imidazole The product of Example 7 [4-(4-Fluorophenyl-5-[(2-(3-benzyloxyphenyl)amino)pyrimidin-4-yl]-(N-carboethoxypiperidin-4-yl)imidazole] was treated according to the procedure of Example 20 (d) of U.S. Pat. No. 5,658,903, to afford the title compound. ES+MS m/z=431 (M++H).

Example 12

4-(4-Fluorophenyl-5-[(2-(4-methoxyphenyl)amino)pyrimidin-4-yl]-1-(piperidin-4-yl)imidazole The title compound was prepared using the general procedure outlined in Example 3 (a) & (b), but substituting 4-methoxyaniline as the aniline component. ES+MS m/z=445 (M++H).

Example 13

4-(4-Fluorophenyl-5-[(2-(3-methoxyphenyl)amino)pyrimidin-4-yl]-1-(piperidin-4-yl)imidazole The title compound was prepared using the general procedure outlined in Example 3 (a) & (b), but substituting 3-methoxyaniline as the aniline component. ES+MS m/z=445 (M++H).

Example 14

4-(4-Fluorophenyl-5-[(2-(2-methoxyphenyl)amino)pyrimidin-4-yl]-1-(piperidin-4-yl)imidazole The title compound was prepared using the general procedure outlined in Example 3 (a) & (b), but substituting 2-methoxyaniline as the aniline component. ES+MS m/z=445 (M++H).

Example 15

4-(4-Fluorophenyl-5-[(2-(3-fluoro-2-methylphenyl)amino)pyrimidin-4-yl]-1-(piperidin-4-yl)imidazole The title compound was prepared using the general procedure outlined in Example 3 (a) & (b), but substituting 3-fluoro-2-methylaniline as the aniline component. ES+MS m/z=447 (M++H).

By methods analogous to those described above for Examples 1 to 15 the following additional compounds may be synthesized;

4-(4-Fluorophenyl-5-[(2-(3-chlorophenyl)amino)pyrimidin-4-yl]-1-(piperidin-4-yl)imidazole;

4-(4-Fluorophenyl-5-[(2-(4-chlorophenyl)amino)pyrimidin-4-yl]-1-(piperidin-4-yl)imidazole;

4-(4-Fluorophenyl-5-[(2-(4-trifluoromethylphenyl)amino)pyrimidin-4-yl]-1-(piperidin-4-yl)imidazole;

4-(4-Fluorophenyl-5-[(2-(3,4-dichlorophenyl)amino)pyrimidin-4-yl]-1-(piperidin-4-yl)imidazole;

4-(4-Fluorophenyl-5-[(2-(4-fluoro-2-methylphenyl)amino)pyrimidin-4-yl]-1-(piperidin-4-yl)imidazole 4-(4-Fluorophenyl-5-[(2-(5-fluoro-2-methylphenyl)amino)pyrimidin-4-yl]-1-(piperidin-4-yl)imidazole;

4-(4-Fluorophenyl-5-[(2-(4-fluoro-2,6-dimethylphenyl)amino)pyrimidin-4-yl]-1-(piperidin-4-yl)imidazole;

4-(4-Fluorophenyl-5-[(2-(4-fluoro-2-chlorophenyl)amino)pyrimidin-4-yl]-1-(piperidin-4-yl)imidazole;

trans 4-(4-Fluorophenyl-5-[(2-(4-fluoro-2-methylphenyl)amino)pyrimidin-4-yl]-1(4-hydroxycyclohexyl)imidazole;

trans 4-(4-Fluorophenyl-5-[(2-(4-fluorophenyl)amino)pyrimidin-4-yl]-1-(4-hydroxycyclohexyl)imidazole;

trans 4-(4-Fluorophenyl-5-[(2-(3-fluoro-2-methylphenyl)amino)pyrimidin-4-yl]-1-(4-hydroxycyclohexyl)imidazole;

trans 4-(4-Fluorophenyl-5-[(2-(5-fluoro-2-methylphenyl)amino)pyrimidin-4-yl]-1-(4-hydroxycyclohexyl)imidazole;

trans 4-(4-Fluorophenyl-5-[(2-(4-fluoro-2-chlorophenyl)amino)pyrimidin-4-yl]-1-(4-hydroxycyclohexyl)imidazole;

cis 4-(4-Fluorophenyl-5-[(2-(4-fluoro-2-methylphenyl)amino)pyrimidin-4-yl]-1-(4-hydroxycyclohexyl)imidazole;

cis 4-(4-Fluorophenyl-5-[(2-(4-fluorophenyl)amino)pyrimidin-4-yl]-1-(4-hydroxycyclohexyl)imidazole;

cis 4-(4-Fluorophenyl-5-[(2-(3-fluoro-2-methylphenyl)amino)pyrimidin-4-yl]-1-(4-hydroxycyclohexyl)imidazole;

cis 4-(4-Fluorophenyl-5-[(2-(5-fluoro-2-methylphenyl)amino)pyrimidin-4-yl]-1-(4-hydroxycyclohexyl)imidazole;

cis 4-(4-Fluorophenyl-5-[(2-(4-fluoro-2-chlorophenyl)amino)pyrimidin-4-yl]-1-(4-hydroxycyclohexyl)imidazole;

trans 4-(4-Fluorophenyl-5-[(2-(4-fluoro-2-methylphenyl)amino)pyrimidin-4-yl]-1-(4-hydroxy-4-methylcyclohexyl)imidazole;

trans 4-(4-Fluorophenyl-5-[(2-(4-fluorophenyl)amino)pyrimidin-4-yl]-1-(4hydroxy-4-methylcyclohexyl)imidazole;

trans 4-(4-Fluorophenyl-5-[(2-(3-fluoro-2-methylphenyl)amino)pyrimidin-4-yl]-1-(4-hydroxy-4-methylcyclohexyl)imidazole;

trans 4-(4-Fluorophenyl-5-[(2-(5-fluoro-2-methylphenyl)amino)pyrimidin-4-yl]-1-(4-hydroxy-4-methylcyclohexyl)imidazole;

trans 4-(4-Fluorophenyl-5-[(2-(4-fluoro-2-chlorophenyl)amino)pyrimidin-4-yl]-1-(4-hydroxy-4-methylcyclohexyl)imidazole;

cis 4-(4-Fluorophenyl-5-[(2-(4-fluoro-2-methylphenyl)amino)pyrimidin-4-yl]-1-(4-hydroxy-4-methylcyclohexyl)imidazole;

cis 4-(4-Fluorophenyl-5-[(2-(4-fluorophenyl)amino)pyrimidin-4-yl]-14-hydroxy-4-methylcyclohexyl)imidazole;

cis 4-(4-Fluorophenyl-5-[(2-(3-fluoro-2-methylphenyl)amino)pyrimidin-4-yl]-1-(4-hydroxy-4-methylcyclohexyl)imidazole;

cis 4-(4-Fluorophenyl-5-[(2-(5-fluoro-2-methylphenyl)amino)pyrimidin-4-yl]-1-(4-hydroxy-4-methylcyclohexyl)imidazole;

cis 4-(4-Fluorophenyl-5-[(2-(4-fluoro-2-chlorophenyl)amino)pyrimidin-4-yl]-1-(4-hydroxy-4-methylcyclohexyl)imidazole.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the are can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound which is:

4-(4-Fluorophenyl)-5-[(2-(4-fluoro-2-methylphenyl)amino)pyrimidin-4-yl]-1-(piperidin-4-yl)imidazole;

4-(4-Fluorophenyl)-5-[(2-(5-fluoro-2-methylphenyl)amino)pyrimidin-4-yl]-1-(piperidin-4-yl)imidazole;

4-(4-Fluorophenyl)-5-[(2-(4-fluoro-2,6-dimethylphenyl)amino)pyrimidin-4-yl]-1-(piperidin-4-yl)imidazole;

4-(4-Fluorophenyl)-5-[(2-(4-fluoro-2-chlorophenyl)amino)pyrimidin-4-yl]-1-(piperidin-4-yl)imidazole;

trans 4-(4-Fluorophenyl)-5-[(2-(4-fluoro-2-methylphenyl)amino)pyrimidin-4-yl]-1-(4-hydroxycyclohexyl)imidazole;

trans 4-(4-Fluorophenyl)-5-[(2-(4-fluorophenyl)amino)pyrimidin-4-yl]-1-(4-hydroxycyclohexyl)imidazole;

trans 4-(4-Fluorophenyl)-5-[(2-(3-fluoro-2-methylphenyl)amino)pyrimidin-4-yl]-1-(4-hydroxycyclohexyl)imidazole;

trans 4-(4-Fluorophenyl)-5-[(2-(5-fluoro-2-methylphenyl)amino)pyrimidin-4-yl]-1-(4-hydroxycyclohexyl)imidazole;

trans 4-(4-Fluorophenyl)-5-[(2-(4-fluoro-2-chlorophenyl)amino)pyrimidin-4-yl]-1-(4-hydroxycyclohexyl)imidazole;

cis 4-(4-Fluorophenyl)-5-[(2-(4-fluoro-2-methylphenyl)amino)pyrimidin-4-yl]-1-(4-hydroxycyclohexyl)imidazole;

cis 4-(4-Fluorophenyl)-5-[(2-(4-fluorophenyl)amino)pyrimidin-4-yl]-1-(4-hydroxycyclohexyl)imidazole;

cis 4-(4-Fluorophenyl)-5-[(2-(3-fluoro-2-methylphenyl)amino)pyrimidin-4-yl]-1-(4-hydroxycyclohexyl)imidazole;

cis 4-(4-Fluorophenyl)-5-[(2-(5-fluoro-2-methylphenyl)amino)pyrimidin-4-yl]-1-(4-hydroxycyclohexyl)imidazole;

cis 4-(4-Fluorophenyl)-5-[(2-(4-fluoro-2-chlorophenyl)amino)pyrimidin-4-yl]-1-(4-hydroxycyclohexyl)imidazole;

trans 4-(4-Fluorophenyl)-5-[(2-(4-fluoro-2-methylphenyl)amino)pyrimidin-4-yl]-1-(4-hydroxy-4-methylcyclohexyl)imidazole;

trans 4-(4-Fluorophenyl)-5-[(2-(4-fluorophenyl)amino)pyrimidin-4-yl]-1-(4-hydroxy-4-methylcyclohexyl)imidazole;

trans 4-(4-Fluorophenyl)-5-[(2-(3-fluoro-2-methylphenyl)amino)pyrimidin-4-yl]-1-(4-hydroxy-4-methylcyclohexyl)imidazole;

trans 4-(4-Fluorophenyl)-5-[(2-(5-fluoro-2-methylphenyl)amino)pyrimidin-4-yl]-1-(4-hydroxy-4-methylcyclohexyl)imidazole;

trans 4-(4-Fluorophenyl)-5-[(2-(4-fluoro-2-chlorophenyl)amino)pyrimidin-4-yl]-1(4-hydroxy-4-methylcyclohexyl)imidazole;

cis 4-(4-Fluorophenyl)-5-[(2-(4-fluoro-2-methylphenyl)amino)pyrimidin-4-yl]-1-(4-hydroxy-4-methylcyclohexyl)imidazole;

cis 4-(4-Fluorophenyl)-5-[(2-(4-fluorophenyl)amino)pyrimidin-4-yl]-1-(4-hydroxy-4-methylcyclohexyl)imidazole;

cis 4-(4-Fluorophenyl)-5-[(2-(3-fluoro-2-methylphenyl)amino)pyrimidin-4-yl]-1-(4-hydroxy-4-methylcyclohexyl)imidazole;

cis 4-(4-Fluorophenyl)-5-[(2-(5-fluoro-2-methylphenyl)amino)pyrimidin-4-yl]-1-(4-hydroxy-4-methylcyclohexyl)imidazole;

cis 4-(4-Fluorophenyl)-5-[(2-(4-fluoro-2-chlorophenyl)amino)pyrimidin-4-yl]-1-(4-hydroxy-4-methylcyclohexyl)imidazole; or a pharmaceutically acceptable salt thereof.

2. A pharmaceutical composition comprising an effective amount of a compound according to claim 1, and a pharmaceutically acceptable carrier or diluent.

3. A method of treating a CSBP/RK/p38 kinase mediated disease in a mammal in need thereof, which method comprises administering to said mammal an effective amount of a compound according to claim 1.

4. The method according to claim 3 wherein the mammal is afflicted with a CSBP/RK/p38 kinase mediated disease selected from psoriatic arthritis, Reiter's syndrome, rheumatoid arthritis, gout, traumatic arthritis, rubella arthritis, acute synovitis, rheumatoid arthritis, rheumatoid spondylitis, osteoarthritis, or gouty arthritis.

5. The method according to claim 3 wherein the mammal is afflicted with a CSBP/RK/p38 kinase mediated disease selected from sepsis, septic shock, endotoxic shock, gram negative sepsis, or toxic shock syndrome.

6. The method according to claim 3 wherein the mammal is afflicted with a CSBP/RK/p38 kinase mediated disease selected from Alzheimer's disease, stroke, neurotrauma, CNS injury, reperfusion injury, restenosis, cardiac and renal reperfusion injury, thrombosis, or glomerularnephritis.

7. The method according to claim 3 wherein the mammal is afflicted with a CSBP/RK/p38 kinase mediated disease selected from asthma, adult respiratory distress syndrome, chronic pulmonary inflammatory disease, silicosis, or pulmonary sarcososis.

8. The method according to claim 3 wherein the mammal is afflicted with a CSBP/RK/p38 kinase mediated disease selected from bone resorption disease, or osteoporosis.

9. The method according to claim 3 wherein the mammal is afflicted with a CSBP/RK/p38 kinase mediated disease selected from diabetes, graft vs. host reaction, or allograft rejection.

10. The method according to claim 3 wherein the mammal is afflicted with a CSBP/RK/p38 kinase mediated disease selected from inflammatory bowel disease, Crohn's disease, ulcerative colitis, multiple sclerosis, muscle degeneration, eczema, contact dermatitis, psoriasis, pyresis, sunburn, conjunctivitis, or cerebral malaria.

11. A method of treating inflammation in a mammal in need thereof, which comprises administering to said mammal an effective amount of a compound according to claim 1.

* * * * *